(12) United States Patent
Fransson et al.

(10) Patent No.: US 6,354,145 B1
(45) Date of Patent: Mar. 12, 2002

(54) PROCESS CONTROL

(75) Inventors: Magnus Fransson; Lars Karlsson, both of Mölndal; Bengt Lagerholm, Kungälv; Anders Sparén, Göteborg, all of (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/355,297

(22) PCT Filed: May 13, 1999

(86) PCT No.: PCT/SE99/00939

§ 371 Date: Jul. 28, 1999

§ 102(e) Date: Jul. 28, 1999

(87) PCT Pub. No.: WO99/63338

PCT Pub. Date: Dec. 9, 1999

(30) Foreign Application Priority Data

Jun. 2, 1998 (SE) .............................. 9801949

(51) Int. Cl.[7] .................. G01N 31/08; B01D 15/08; G01F 1/12
(52) U.S. Cl. .................. 73/61.52; 73/61.57; 73/23.1; 210/198.2; 702/32
(58) Field of Search ................ 73/61.52, 61.57, 73/61.41, 23.21, 23.36, 61.43, 61.44; 210/198.2; 702/32

(56) References Cited

U.S. PATENT DOCUMENTS

| | | | | |
|---|---|---|---|---|
| 4,357,668 A | * | 11/1982 | Schwartz et al. | 364/497 |
| 4,875,169 A | * | 10/1989 | Synovec et al. | 364/497 |
| 4,927,532 A | * | 5/1990 | Pospisil et al. | 210/198.2 |
| 4,941,101 A | * | 7/1990 | Crilly | 364/497 |
| 5,150,061 A | * | 9/1992 | Castel et al. | 324/640 |
| 5,266,191 A | * | 11/1993 | Green et al. | 210/195.1 |
| 5,396,806 A | * | 3/1995 | Dechene et al. | 73/861.04 |
| 5,473,934 A | * | 12/1995 | Cobb | 73/61.49 |
| 5,524,084 A | * | 6/1996 | Wang et al. | 364/510 |
| 5,708,211 A | * | 1/1998 | Jepson et al. | 73/861.04 |
| 5,736,637 A | * | 4/1998 | Evans | 73/152.31 |
| 5,795,996 A | * | 8/1998 | Chang et al. | 73/61.41 |
| 6,167,965 B1 | * | 1/2001 | Bearden et al. | 166/250.15 |

FOREIGN PATENT DOCUMENTS

| | | |
|---|---|---|
| EP | 0396884 | 11/1990 |
| WO | 9963338 | 12/1999 |

OTHER PUBLICATIONS

Guillemin, C. L. Laboratory Information Management, 17(1992) 201–211.
Nomikos, P. MacGregor, J. F. Technometrics, Feb. 1995, vol. 37, No. 1, 41–59.

* cited by examiner

Primary Examiner—Hezron Williams
Assistant Examiner—David J. Wiggins
(74) Attorney, Agent, or Firm—White & Case LLP

(57) ABSTRACT

The present invention relates to a method for analyzing mixtures of components by a process selected from the group consisting of flow based separation processes and flow analysis processes. The method comprising the steps of:

obtaining measurement signals by measuring process conditions at a plurality of positions throughout the system;

applying signal processing to the measurement signals, said signal processing comprising multivariate data analysis for condensing the plurality of measurement signals to a smaller number of main signals being non-correlated;

logging said main signals; and displaying said main signals versus time, where changes of said system conditions are indicated by one or more of the displayed main signals;

detecting any error occurrence during an on going process, and determining what part of said system cause said error.

13 Claims, 5 Drawing Sheets

PROCESS CONTROL

TECHNICAL FIELD

The present invention relates to a method for monitoring a process and more specifically it relates to monitoring flow based separation processes and/or flow analysis processes for analyzing mixtures of components.

TECHNICAL BACKGROUND

Examples of the above processes are; liquid chromatography (LC); gas chromatography (GC), capillary electrophoresis (CE), capillary electrochromatography (CEC), supercritical fluid chromatography (SFC), which are all flow based separation processes, and flow injection analysis (FIA) and continuous flow analysis (CFA), which are flow analysis processes. Such processes are used for analyzing the concentration of different components of mixtures, such as pharmaceuticals. These processes are among other things used for their high degree of accuracy and their ability to disclose low concentrations. On the other hand, these features lead to demands for high stability for the results to be trustworthy. Hence, different methods of monitoring the processes in order to secure the stability and, thus, the accuracy of the results have been developed.

One prior art method is disclosed in U.S. Pat. No. 5,524,084, where the inlet fluid flow of a gas chromatograph is controlled by measuring mass fluid flow, fluid pressure and temperature in the pneumatic manifold of the inlet, that is before the column. By means of the measurements, fluctuating pressure and temperature are compensated for by controlling the fluid flow, thereby to achieve as constant conditions for the chromatography process as possible.

A rising pressure may indicate an obstruction of the injector, the precolumn, the column, or a fluid tube connected thereto. Such an obstruction could cause many other problems not solved by merely compensating for the increase of the pressure as is done in this prior art. By using this prior art method, there is an apparent risk for causing damage to the system because of a lack of investigation of the cause for the pressure increase. Further, merely compensating for temperature and pressure fluctuations on the inlet side of the system does not cover all states that may arise in the process. Thus, there is still no guarantee that the result remains stable and accurate. Therefore, it is often used in combination with a stability check. This check is performed by running a standard, i.e. a known substance giving a known result, through the system consecutive to a substance to be analyzed. If, for example, a series of 20 samples is to be analyzed, usually one standard is run for every three samples. This is time consuming and involves excessive costs.

Another prior art method is disclosed in a paper entitled Intelligent Instrumentation: Application to On-Line Gas and Liquid Process Chromatography, published in Laboratory Information Management, Vol. 17, No. 2, pp 201–211, November 1992, by C. L. Guillemin. This method analyses the result of the process, i.e. the chromatogram, where each peak corresponds to a different substance and where the area encompassed by the peak corresponds to the concentration. In order to be able to correctly interpret the amounts, a deferred standard concept is used. This means that a standard having a known and relatively long passage time through the column is injected into the system just after the sample is injected and used as a reference. Thereby fluctuations of the peak of the standard are used for adjusting the whole chromatogram accordingly.

This method suffers from the delayed detection of an error, which is not detected until the process is finished and the chromatogram analysis has been performed. Further, a drift of the system, specifically a flat one, is difficult or impossible to detect but may in the long run be detrimental to the performance of the system.

The above described prior art methods could of course be combined in order to improve the stability monitoring. However, there would still be a major drawback of such a combined method as well as of the separate methods what is a difficulty to detect several different types of errors and also to trace the cause of an error and determine what part of the system causes the error.

SUMMARY OF THE INVENTION

An object of the present invention is to provide a method for monitoring flow based analytical separation processes and/or flow analysis processes that facilitates error tracing and makes it possible to detect an error occurrence during an ongoing process.

The object is achieved by a method set out in claim 1 comprising the steps of:

obtaining measurement signals by measuring process conditions at a plurality of positions throughout the system;

applying signal processing to the measurement signals, said signal processing comprising multivariate data analysis for condensing the plurality of measurement signals to a smaller number of main signals being non-correlated;

logging said main signals; and displaying said main signals versus time, where changes of said system conditions are indicated by one or more of the displayed main signals.

The method of this invention significantly facilitates the tracing of errors affecting the system stability and giving rise to unusable results of the analyses. Further, by monitoring the system at several vital positions, and thereby substantially improving the robustness and reliability of the analysis, the need for using standards as system calibrators is dramatically reduced. Thus, time that so far has been occupied by handling standards is released for mixture analysis.

The method of this invention is carried out by an apparatus according to claim 7, whereby the apparatus comprises:

means for measuring process conditions at a plurality of positions throughout the system; and means for processing signals from said measuring means, said signal processing means comprising multivariate data analysis for condensing the plurality of measurement signals to a smaller number of main signals being non-correlated; and means for logging said main signals; and means for displaying said main signals versus time, where changes of said process conditions are indicated by one or more of the displayed main signals.

Further aspects and advantages of the present invention will become apparent from the dependent claims and by the following detailed description, taken in conjunction with the accompanying drawings.

SHORT DESCRIPTION OF THE DRAWINGS

Figure 3:
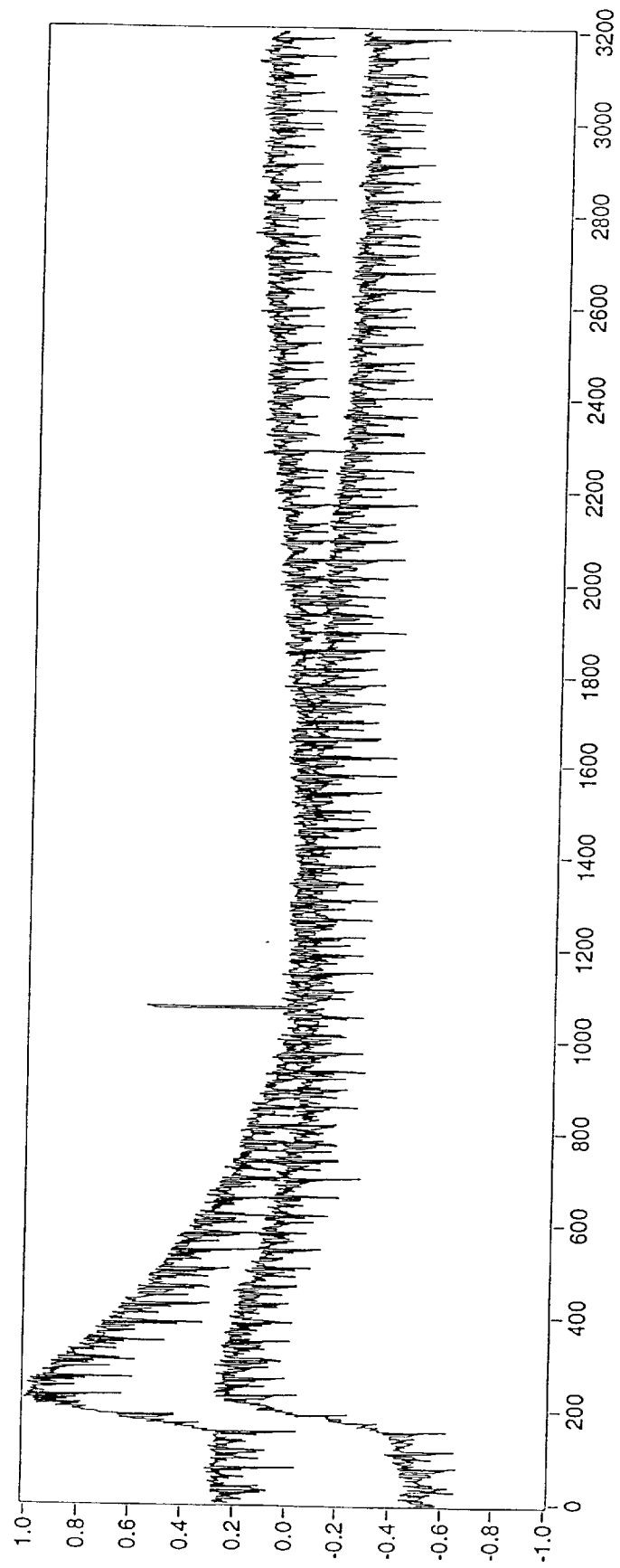

FIG. 3 discloses a score vector plot.

Figure 4:
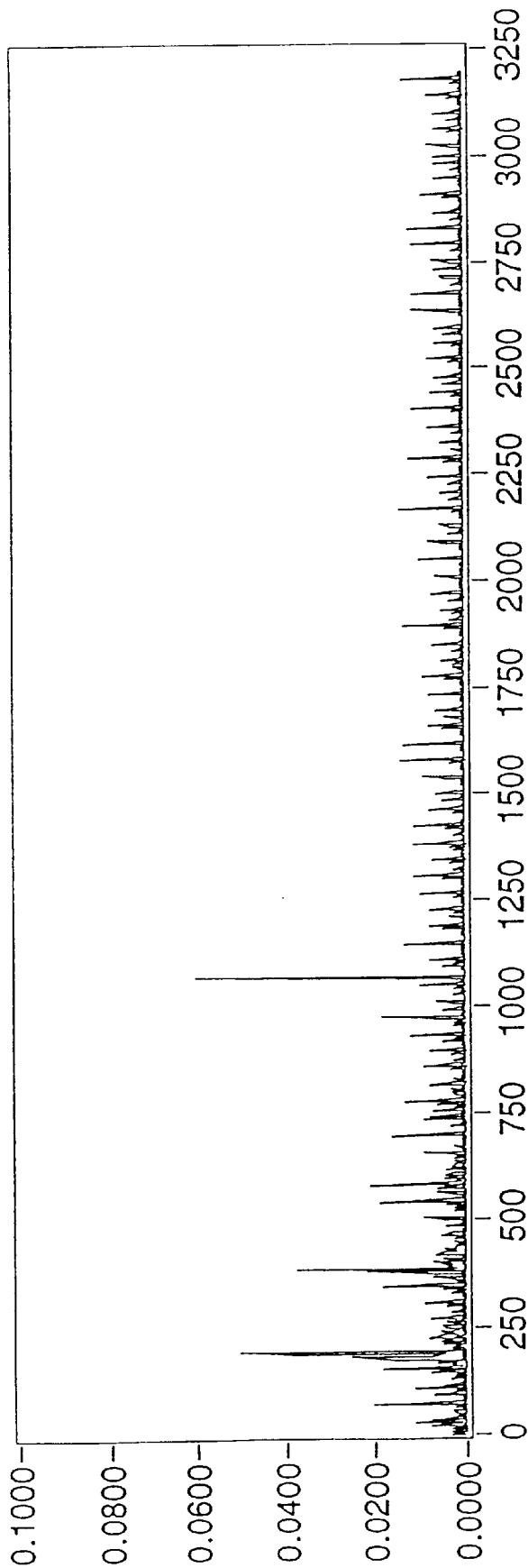

FIG. 4 discloses a DModX plot.

Figure 1:
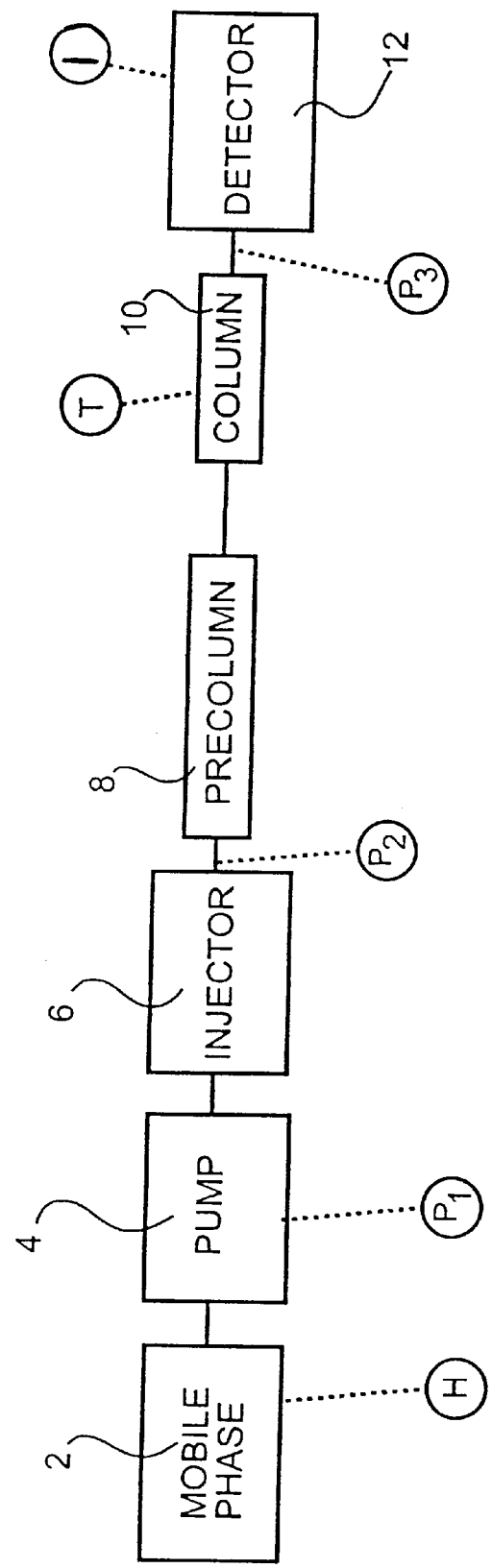
FIG. 1 illustrates schematically an apparatus employing an embodiment of the method according to the present invention.
Figure 2:
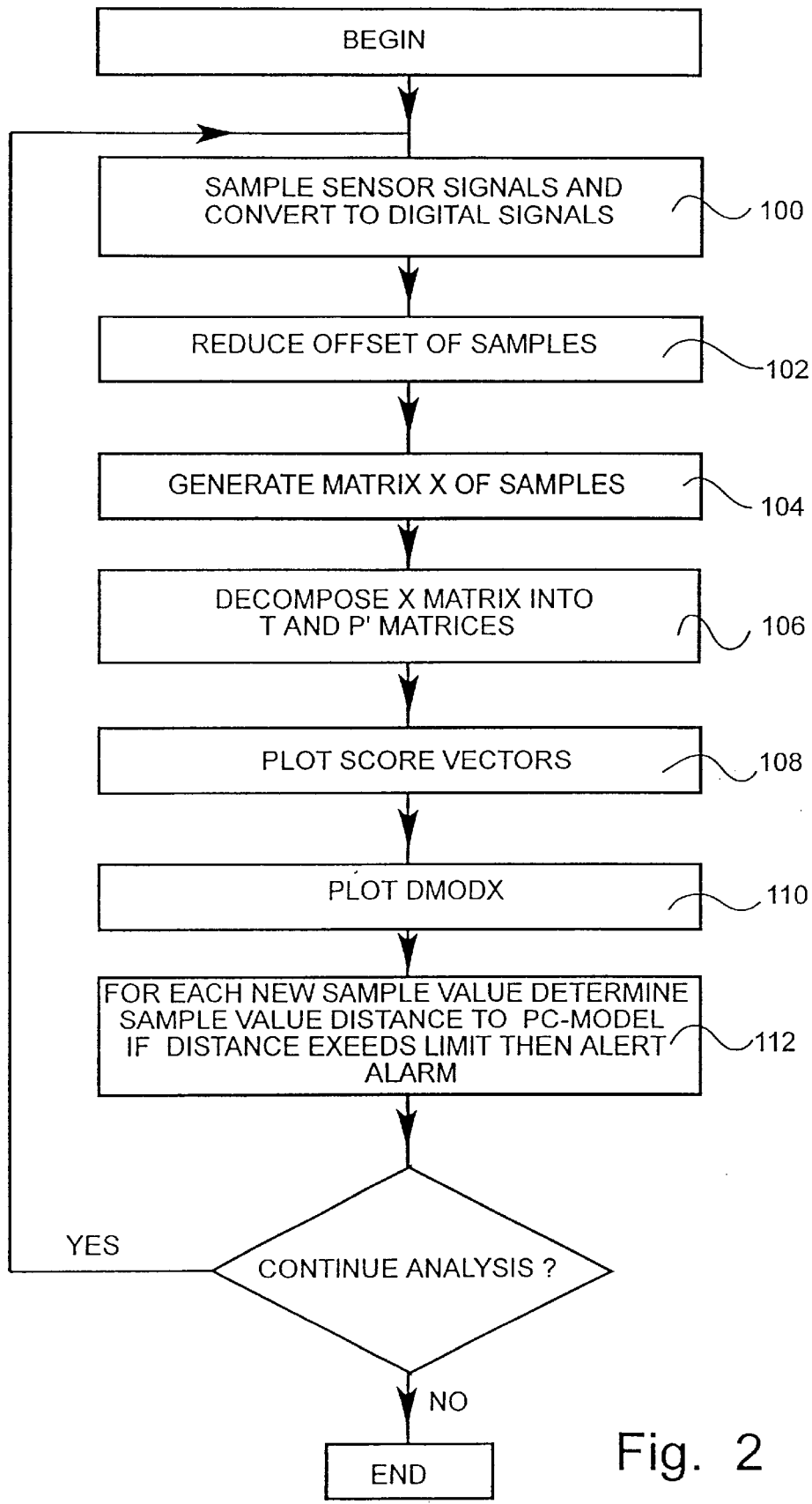
FIG. 2 is a flow chart of an embodiment of the method of the present invention.
Figure 5:
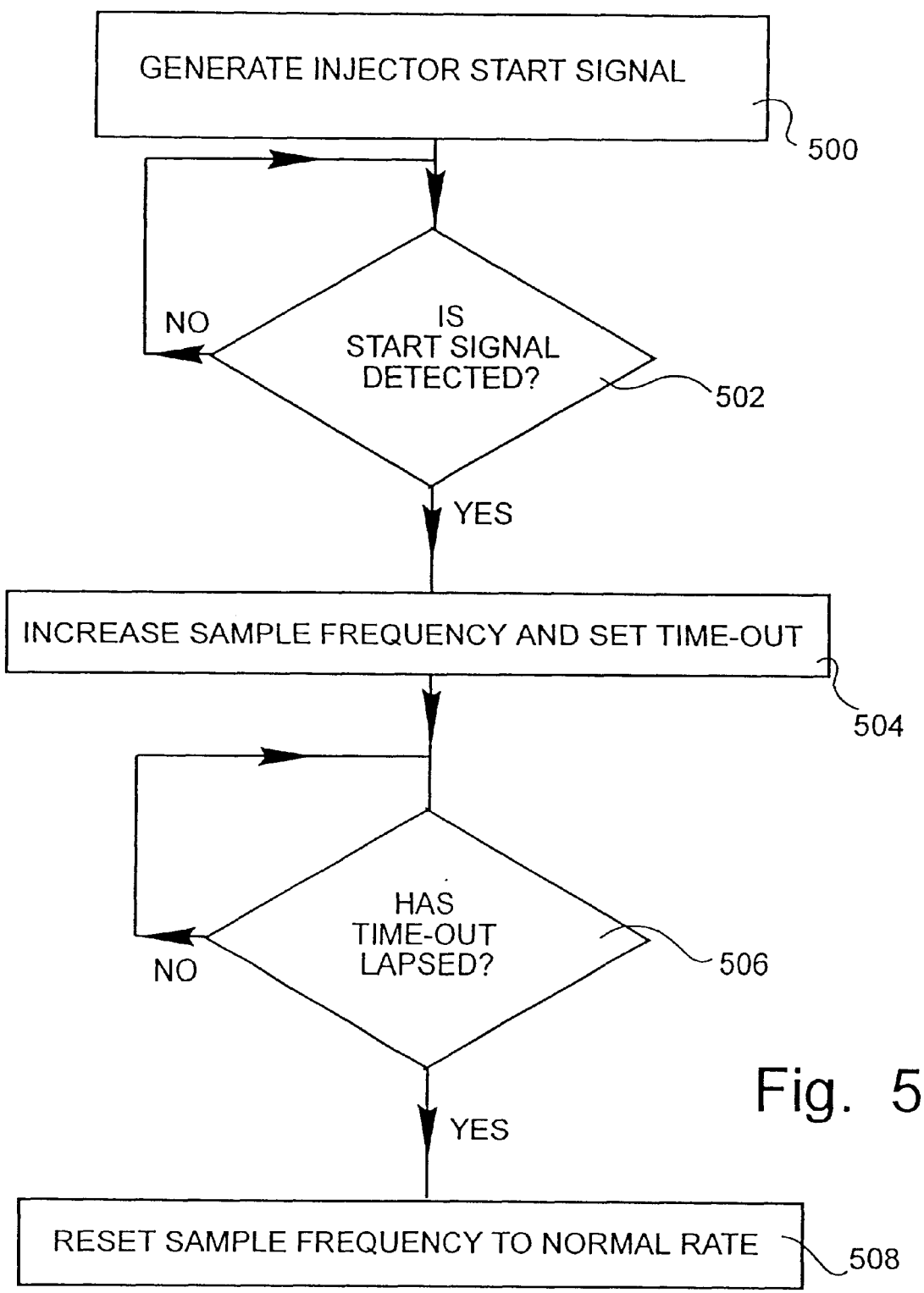

FIG. 5 is a flow chart of a modification of the embodiment of FIG. 2.

DESCRIPTION OF EMBODIMENTS

The present invention provides a method for monitoring flow based analytical separation processes and/or flow analysis processes. In the following the invention will be exemplary described as applied on a liquid chromatography process. It is of course equally applicable to other processes comprised in the above mentioned groups.

A conventional liquid chromatograph comprises a mobile phase 2, a pump 4, an injector 6, a precolumn 8, a column 10 and a detector 12. The detector is a UV light detector. Alternatively, two or more separate pumps may be used for creating mobile phase gradients, allowing a continuous change in mobile phase composition during a run. In the application illustrated on the drawing, however, the method is applied to an isocratic, i.e. constant mobile phase composition, set-up.

The mobile phase 2 is continuously pumped through the system by means of the pump 4. By means of the injector 6 the mixture to be analysed is added to and dissolved into the mobile phase 2, which performs the function of a solvent. In the precolumn, particles that do not elute from the column are trapped. Thereby, the life time of the analytical column is extended. In the column the components of the mixture are separated, while passing through at different speeds. The components are detected by the detector and a chromatogram is plotted presenting a separate peak for each of the components.

The accuracy of the analysis is high and since this process often is used for analysis of pharmaceutical mixtures where the concentrations of different components need to be held within narrow limits, it is essential that the result of the analysis is reliable. Thus, there is a need for keeping the process stable. The method of the present invention is advantageously employed for monitoring such demanding processes. Features strongly affecting the stability are for example the temperature of the column and the function of the detector. The pressure at different positions of the system is also of importance; however even more importantly the pressure is an indicator of the performance of the system and of different parts of the system. In accordance with this embodiment of the invention the pressure is measured in the pump, before the precolumn and after the column. Sensors for detecting the pressure are applied and denoted by $P_1$, $P_2$ and $P_3$ respectively. Further, the temperature of the column is measured by means of a sensor T, the current through the UV lamp of the detector 12 is measured by a current sensor I, and the pH of the mobile phase is measured by means of a pH-meter H.

All these signals are generated in order to monitor the analysis process, thereby to secure that the system is stable during the analysis. This ensures a high analytical quality of the resulting chromatogram. The measurement signals obtained from the sensors $P_1$–$P_3$, T, I and H are continuously logged as will be described in greater detail below. Any change in the system is detected and logged in relation to time. Thus, it is possible to determine at what time the change occurred. Since the most critical parameters are measured and at strategic positions in the system, it is possible also to determine what happened and where in the system it happened as well.

However, six different signals are far too many for a human operator to take in, particularly since several thereof are more or less correlated. Hence, there has to be some way to condense their inherent information. In accordance with the invention the solution is to employ Multivariate Data Analysis (MVDA) in order to condense the information of the signals into fewer ones, preferably non-correlated. The basic MVDA methods are known per se, but up till now no one has perceived that they could be useful within this technological field. In the following, the application of these methods will be explained.

The six measurement signals, generated by the sensors $P_1$–$P_3$, T, I, and H, in a first step denoted 100 are sampled in parallel. Thus, each sample contains six different sample values, which are then subjected to signal processing by means of MVDA. These methods comprise a method referred to as Principal Component Analysis (PCA), which is applied in this embodiment. In PCA a plurality of variables are approximated with fewer ones, preferably two, referred to as principal components. These principal components capture the main features of the signals and are non-correlated. Thus, as an introduction to the PCA, in a third step 104 the sample values are arranged in a matrix X, where each row represents a different sample and each column represents a different signal. In order to reduce offset of the sample values, in a second step 102 a mean of all previous sample values of a signal is subtracted from each new sample value of that signal before said new sample value is introduced into the matrix X. Thereby, the values of all signals are centered in a multidimensional co-ordinate system constituted by the matrix columns.

Then, in a step 106, the matrix X is approximated in terms of the product of two smaller matrices T and P'. These matrices capture the essential patterns of X. A complete decomposition of X could be expressed as X=TP'+E, where E is a noise matrix. If X is a 100×6 matrix, i.e. 100 samples, then T is a 100×2 matrix, i.e. two principal components, and P' is a 2×6 matrix. E is a 100×6 matrix. Mathematically what is done when decomposing the matrix X is to project a 6-dimensional space on a 2-dimensional space, and the determination of the matrices T and P' is based on minimizing the matrix E by means of least square calculations. Thus, the Principal Component model (PC-model) is a plane that is spanned by the two columns of the matrix T.

Then, in a step 108, the columns of T, t1 and t2, which are called score vectors, are plotted, as illustrated in FIG. 3. This score vector plot, below referred to as the total plot, is updated continuously every N samples, where N is a predetermined number, e.g. 200 or 400. Thus, the PCA generating said score vectors is performed on an ever-increasing X matrix including all samples from the beginning of the analysis.

In a step 110, a distance-to-model (DModX) plot is made, as illustrated in FIG. 4. This is a plot of the residuals of t1 and t2 respectively, determined as the standard deviation of the noise matrix E. More particularly, for each sample, having determined t1, a residual r1 is determined and, having determined t2, a residual r2 is determined. However, by contrast with the total plot, the updating of the DModX plot, i.e. the calculation of t1, t2, r1 and r2 as a basis for the DModX plot, is not based on all previous samples but on the last N samples. N is a predetermined number of samples, e.g. 200 or 400. That is, for each new batch of N samples the calculation is made and the DModX plot is updated. On the other hand, the DModX plot as a whole preferably displays the whole history of the analysis, just like the total plot does.

If drift occurs somewhere in the system, this appears clearly from the total plot as a deviation, whereas sudden disturbances are best seen in the DModX plot. Thus, in fact the instrumentation performance is monitorable in real-time. Since the score vectors are non-correlated, a deviation of the system behavior may appear in a single one of the graphs t1, t2, while the other is unaffected. From simple tests, where different types of errors are simulated at different positions of the system, it is possible to gain experience, from what types of indications are related to what problems. Having gained that experience a user of this method will be able to rather quickly find the cause of the deviation. This is a substantial enhancement over the existing methods, where error tracing is very time consuming and expensive.

Then, in a step 112, the distance from each separate value of the present sample to the PC-model is determined. The distance is measured along an orthogonal projection of the value on the PC-model. If the distance exceeds a predetermined limit an alarm, e.g. a lamp, is alerted.

Since all data, i.e. the samples as well as the generated matrices, are all stored it is possible to backlog not only the total and DModX plots but also every single sensor signal in order to find the exact time and position of the occurrence of a fault or a disturbance. Thus, the means for and possibilities to perform fault tracing are substantially improved in relation to the prior art methods. It is often possible to determine in short time what part of the system is erroneous simply by evaluating the plots in conjunction with the signal data. The two PCA-derived plots are preferably used for determining at what time an occurrence took place and by studying the signal data at that time it is often possible to determine where in the system the occurrence took place.

Above a preferred embodiment of the method according to the present invention has been described. This should be seen as merely a non-limiting example. Many modifications will be possible within the scope of the invention as defined by the claims. Below a few examples of such modifications will be given.

For example, as a complement to the plots of FIGS. 3 and 4, plots of raw data, i.e. the very sample values, from the different sensors could be provided on the monitor. Thereby, one could swiftly scan those plots for discontinuities being timed with a error indication of any of the PCA-derived plots. Thus, while the PCA-derived plots efficiently indicate a deviation, the raw data plots are usable for finding the cause of the deviation. Consequently, this method is also useful for monitoring the function of different parts of the system.

The action of injecting the mixture into the solvent is particularly critical, and it is very important that this is done in exactly the same way every time, especially when performing a consecutive series of analyses. Referring now to FIG. 5, as another modification, the method includes the following steps. In a step 500, the injector 6 generates a signal indicating that an injection is to be performed in short. Then, in a step 502, the signal is detected. Upon the signal detection the sample frequency is increased and a time out is set in a step 504. The sample frequency is kept at the increased rate for a short time period that covers the lapse of the injection and some moments following the injection. When the time-out has lapsed, in a step 506, the sample frequency is reset to the normal rate, in step 508. By this momentarily increased resolution the performance of the injector is monitorable in detail.

Of course, the invention is not limited to the above six sensor signals. If useful in a certain application, their number could be optionally expanded. For instance, using modern sensor technology, several temperature and/or flow measurements could be done in-line at various positions of the system. By multivariate analysis, they would be similarly condensed to a few non-correlated signals. The number of principal components, or other types of similarly determined signals, may be chosen both fewer and more in accordance with known techniques. However, two is often an optimal choice.

Other MVDA methods than PCA could be used, such as SVD, singular Value Decomposition, or PLS, Partial Least Squares.

What is claimed is:

1. A method for analyzing mixtures of components by a monitoring process selected from the group consisting of flow based separation processes and flow analysis processes, in a system the method comprising the steps of:

obtaining measurement signals by measuring process conditions at a plurality of positions throughout the system;

applying signal processing to the measurement signals, said processing comprising multivariate data analysis for condensing the plurality of measurement signals to a smaller number of main signals being non-correlated;

logging said main signals;

displaying said main signals versus time, where changes of said system conditions are indicated by one or more of the displayed main signals;

detecting any error occurrence during an ongoing process; and determining what part of said system caused said error.

2. The method according to claim 1, wherein the step of signal processing comprises the steps of:

sampling the measurement signals; and employing different sampling frequencies at different process steps of the analysis.

3. A method for analyzing mixtures of components by a process selected from the group consisting of flow based separation processes and flow analysis processes in a system, the method comprising the steps of:

obtaining measurement signals by measuring process conditions at a plurality of positions throughout the system;

applying signal processing to the measurement signals, said signal processing comprising multivariate data analysis for condensing the plurality of measurement signals to a smaller number of main signals being non-correlated;

logging said main signals;

displaying said main signals versus time, where changes of said system conditions are indicated by one or more of the main signals displayed;

detecting any error occurrence during an ongoing process; and determining what part of said system caused said error; and wherein the multivariate data analysis comprises principal component analysis and that at least two principal components are determined and displayed in two different diagrams, one diagram thereof adopted to particularly disclose drift of the system conditions, and another diagram adopted to particularly disclose abrupt or short time deviations of the system conditions.

4. A method for analyzing mixtures of components by a process selected from the group consisting of flow based separation processes and flow analysis processes in a system, the method comprising the steps of:

obtaining measurement signals by measuring process conditions at a plurality of positions throughout the system;

applying signal processing to the measurement signals, said signal processing comprising multivariate data analysis for condensing the plurality of measurement signals to a smaller number of main signals being non-correlated;

logging said main signals;

displaying said main signals versus time, wherein changes of said system conditions are indicated by one or more of the main signals displayed;

detecting any error occurrence during an ongoing process; and determining what part of said system caused said error;

wherein the flow analysis process is a liquid chromatography process having a system comprising a pump, a precolumn, a column, and a detector; wherein the pump is pressurized, a pressure is maintained before the precolumn, the column has a temperature, and the detector has a current passing therethrough, and said measurement signals comprise the pressure of the pump, the pressure before the precolumn, the temperature of the column, and the current of the detector.

5. The method according to claim 1, wherein the mixture comprises pharmaceutical substances.

6. An apparatus for analyzing mixtures of components by a monitoring process selected from the group consisting of flow based separation processes and flow analysis processes, the apparatus comprising:

means for measuring process conditions at a plurality of positions throughout the system;

means for processing signals from said measuring means, said signal processing means comprising multivariate data analysis for condensing the plurality of measurement signals to a smaller number of main signals being non-correlated;

means for logging said main signals;

means for displaying said main signals versus time, where changes of said process conditions are indicated by one or more of the displayed main signals;

means for detecting any error occurrence during an ongoing process; and means for determining what part of said system caused said error.

7. The apparatus according to claim 6, wherein said means for measuring process conditions comprises at least sensor.

8. The apparatus according to claim 7, wherein said at least one sensor is a pressure sensor.

9. The apparatus according to claim 7, wherein said at least one sensor is a temperature sensor.

10. The apparatus according to claim 7, wherein said at least one sensor is a current sensor.

11. The apparatus according to claim 7, wherein said at least one sensor is a pH-meter.

12. The apparatus according to claim 7, wherein the preferred number of sensors is six.

13. The apparatus according to claim 12, wherein three of the sensors are pressure sensors.

* * * * *

UNITED STATES PATENT AND TRADEMARK OFFICE
CERTIFICATE OF CORRECTION

PATENT NO. : 6,354,145 B1
DATED : March 12, 2002
INVENTOR(S) : Fransson et al.

It is certified that error appears in the above-identified patent and that said Letters Patent is hereby corrected as shown below:

<u>Title page,</u>
Item [22], change "13" to -- 31 --.

<u>Column 8,</u>
Line 17, insert -- one -- after "at least."

Signed and Sealed this

Seventeenth Day of September, 2002

Attest:

Attesting Officer

JAMES E. ROGAN
*Director of the United States Patent and Trademark Office*